United States Patent [19]
Godik

[11] Patent Number: 5,699,797
[45] Date of Patent: Dec. 23, 1997

[54] METHOD OF INVESTIGATION OF MICROCIRCULATION FUNCTIONAL DYNAMICS OF PHYSIOLOGICAL LIQUIDS IN SKIN AND APPARATUS FOR ITS REALIZATION

[75] Inventor: Eduard E. Godik, Washington Township, N.J.

[73] Assignee: Dynamics Imaging, Inc., Devon, Pa.

[21] Appl. No.: 411,644

[22] PCT Filed: Oct. 4, 1993

[86] PCT No.: PCT/US93/09480

§ 371 Date: Aug. 14, 1995

§ 102(e) Date: Aug. 14, 1995

[87] PCT Pub. No.: WO94/07408

PCT Pub. Date: Apr. 14, 1994

[30] Foreign Application Priority Data

Oct. 5, 1992 [RU] Russian Federation ......... 5064982

[51] Int. Cl.$^6$ .................................................. A61B 5/05
[52] U.S. Cl. ................. 128/653.1; 128/664; 128/665; 128/633
[58] Field of Search ................. 128/653.1, 664, 128/665, 633; 250/330, 341

[56] References Cited

U.S. PATENT DOCUMENTS

| 3,878,392 | 4/1975 | Yew et al. ............... 250/306 |
| 3,897,150 | 7/1975 | Bridges et al. ............... 356/5 |
| 4,212,306 | 7/1980 | Mahumud ............... 128/665 |
| 4,281,645 | 8/1981 | Jöbsis ............... 128/633 |
| 4,286,602 | 9/1981 | Guy ............... 128/665 |
| 4,312,357 | 1/1982 | Andersson et al. ............... 128/664 |
| 4,385,634 | 5/1983 | Bowen ............... 128/653 |
| 4,495,949 | 1/1985 | Stoller ............... 128/664 |
| 4,515,165 | 5/1985 | Carroll ............... 128/664 |
| 4,536,790 | 8/1985 | Kruger et al. ............... 358/111 |
| 4,570,638 | 2/1986 | Stoddart et al. ............... 128/665 |
| 4,576,173 | 3/1986 | Parker et al. ............... 128/633 |
| 4,583,869 | 4/1986 | Chive et al. ............... 374/122 |
| 4,649,275 | 3/1987 | Nelson et al. ............... 250/358.1 |
| 4,767,928 | 8/1988 | Nelson et al. ............... 250/341 |

(List continued on next page.)

FOREIGN PATENT DOCUMENTS

0447708A3  9/1991  European Pat. Off. .
WO79/00594  8/1979  WIPO .

OTHER PUBLICATIONS

Godik, E.E., Guljaev, Yu.V., "The Human Being Through 'Eyes of Radiophysics'", *Journal of Radio Engineering* (Russian) 1991, No. 8, pp. 51–56.

Ring, E.F.J. and Hughes, H. "Real Time Video Thermography", in *Recent Developments in Medical and Physiological Imaging* a supplement to *Journal of Medical Engineering and Technology*, 1986, pp.86–89.

Platonov, S.A., ..., Godik, E.E., "Informative Tasks of Functional Mapping of Biological Subjects", *Journal of Radio Engineering* (Russian) 1991, No. 8, pp. 62–68.

(List continued on next page.)

*Primary Examiner*—Brian L. Casler
*Attorney, Agent, or Firm*—Jacob N. Erlich; Jerry Cohen

[57] ABSTRACT

This method and apparatus characterizes the interconnection between blood content and capillary blood flow and accomplishes a functional diagnosis of microcirculation of physiological liquids in the skin. In this invention there is a sequential recording of the IR radiation emitted by the skin with simultaneous recording of backscattered electromagnetic radiation at visible and near IR wavelengths under conditions of external illumination over the same region with subsequent superimposition of the images obtained thereby. The parameter to be measured is the relationship between the temporal changes in backscattered electromagnetic radiation in at least one of the spectral ranges of 0.3 to 2.0 µm and changes in intensity of emitted IR radiation. This parameter is represented in the form of spatial-temporal distribution within the boundaries of the image region under investigation.

23 Claims, 9 Drawing Sheets

U.S. PATENT DOCUMENTS

| | | |
|---|---|---|
| 4,798,209 | 1/1989 | Klingenbeck et al. .................. 128/653 |
| 4,810,875 | 3/1989 | Wyatt ........................................ 250/227 |
| 4,817,038 | 3/1989 | Knoll et al. ......................... 364/413.24 |
| 4,817,622 | 4/1989 | Pennypacker et al. .................. 128/664 |
| 4,821,117 | 4/1989 | Sekiguchi ................................ 128/665 |
| 4,829,184 | 5/1989 | Nelson et al. ......................... 250/358.1 |
| 4,862,894 | 9/1989 | Fujii ......................................... 128/666 |
| 4,927,244 | 5/1990 | Bahr et al. ............................ 350/350 S |
| 4,945,239 | 7/1990 | Wist et al. ............................ 250/358.1 |
| 4,948,974 | 8/1990 | Nelson et al. ....................... 250/358.1 |
| 4,955,383 | 9/1990 | Faupel .................................. 128/653 R |
| 4,995,398 | 2/1991 | Turnidge ................................. 128/668 |
| 5,079,698 | 1/1992 | Grenier et al. ...................... 364/413.13 |
| 5,099,848 | 3/1992 | Parker et al. ........................ 128/661.07 |
| 5,139,025 | 8/1992 | Lewis et al. ............................. 128/665 |
| 5,170,119 | 12/1992 | Sekihara et al. ......................... 324/260 |
| 5,197,470 | 3/1993 | Helfer et al. ............................. 128/634 |
| 5,213,105 | 5/1993 | Gratton et al. ........................... 128/664 |
| 5,222,495 | 6/1993 | Clarke et al. ............................ 128/633 |
| 5,269,325 | 12/1993 | Robinson et al. ..................... 128/653.1 |
| 5,293,873 | 3/1994 | Fang ........................................ 128/664 |
| 5,301,681 | 4/1994 | DeBan et al. ........................... 128/736 |
| 5,303,026 | 4/1994 | Strobl et al. ............................. 356/318 |
| 5,305,748 | 4/1994 | Wilk ..................................... 128/653.1 |
| 5,307,807 | 5/1994 | Valdes Sosa et al. ................ 128/653.1 |
| 5,309,907 | 5/1994 | Fang et al. .............................. 128/633 |
| 5,311,018 | 5/1994 | Zana et al. ............................... 250/330 |
| 5,313,941 | 5/1994 | Braig et al. .............................. 128/633 |
| 5,333,610 | 8/1994 | Hirao ....................................... 128/633 |
| 5,337,745 | 8/1994 | Benaron .................................. 128/633 |
| 5,361,758 | 11/1994 | Hall et al. ................................ 128/665 |
| 5,363,854 | 11/1994 | Martens et al. ......................... 128/665 |
| 5,371,368 | 12/1994 | Alfano et al. ......................... 250/341.1 |
| 5,408,996 | 4/1995 | Salb ........................................ 128/665 |
| 5,445,157 | 8/1995 | Adachi et al. ........................... 128/665 |
| 5,452,723 | 9/1995 | Wu et al. ................................. 128/665 |
| 5,572,996 | 11/1996 | Doiron et al. ........................... 128/633 |

OTHER PUBLICATIONS

Jacquez, J.A. et al, "Spectral Reflectance of Human Skin in the Region 235—1000 nm", *Journal of Applied Physiology*, 1955, vol. 7, No. 3, pp. 523–528.—copy not available.

"Physics of Image Visualization in Medicine", C. Webb, ed. vol. 2, pp. 241–243.—copy not available.

Krenkel, T.E., Kogan, A.G. and Tatatorian, A.M., "Personal Computers in Engineering", Izd. Mir, RiS, (Russian) 1989, p. 71.—copy not available.

Dgagupov, R.G. and Erofeev, A.A., *Piezo–Ceramic Elements in Instrument Designing and Automatics*, Leningrad, Izd. Mashinosroenie, 1986, pp. 154–155 (Russian).—copy not available.

Legett, Kate*, *Optical mamography offers promise as alternative to x-ray detection*, Biophotonics International, Jan./Feb., 1996, pp. 56–57.

Godik, Eduard E. and Gulyaev, Uri, V., "Functional Imaging of the Human Body," *IEEE Engineering in Medicine and Biology*, Dec. 1991, pp. 21–29.

METHOD OF INVESTIGATION OF MICROCIRCULATION FUNCTIONAL DYNAMICS OF PHYSIOLOGICAL LIQUIDS IN SKIN AND APPARATUS FOR ITS REALIZATION

CROSS REFERENCE TO RELATED APPLICATIONS

This application claims priority of PCT application PCT/US93/09480 filed Oct. 4, 1993 and Russian application 5,064,982 filed Oct. 5, 1992.

FIELD OF THE INVENTION

The invention relates generally to the field of medicine, and more particularly to methods and apparatus designed to obtain information on physiological processes in living organisms. This information, obtained in a timely and non-invasive fashion, could be used to diagnose a variety of pathological conditions. Because of its non-invasive nature, this invention would be ideal for population screening and preventative medicine.

BACKGROUND OF THE INVENTION

Functional dynamics of the microcirculation of physiological liquids such as blood, lymph or water in the skin reflects the general functioning of the main distributed physiological systems. These systems include cell metabolism, which reflects the efficiency with which energy is used, and microcirculation, which transports resources to the cell and carries away metabolic by-products. The functional status of these systems is determined by distributed regulatory mechanisms: both humoral, which reflect the state of the entire organism, and local, which reflect the state of the local cell metabolism. Cell metabolism is connected with microcirculation via another important distributed tissue system, that of perfusion. The functional dynamics of cell membrane perfusion is a measure of the interconnection between cell metabolism and microcirculation.

The state of the whole-organism regulatory systems is reflected not only by the tissue functional dynamics at separate points of the living organism, but mainly in the degree and character of the spatial connectivity of these dynamics. To reveal this connectivity, it is necessary to perform continuous investigation of microcirculation functional dynamics and cell metabolism. For instance, at a state of relaxation, the spatial connectivity is minimal, while under stress it is greatly increased. For malignant tissues an increased connectivity is typical as compared with the surrounding normal tissues. The state of the whole-organism's systems and organs is reflected in the spatial organization of the organism's tissue functioning, since these systems evolved to support the tissue's functional status.

Modern methods of living organism physical field recording makes it possible to follow the dynamics of these complicated physiological processes. These fields include firstly those characterizing the dynamic temperature "portrait" of the organism: radio-thermal, acousto-thermal and infrared radiation of the skin as described in Godik, E. E., Guljaev, Yu. V., "The Human Being Through 'Eyes of Radiophysics'", Journal of Radio Engineering (Russian) 1991, No. 8, pp. 51–56. Each of the these types of radiation conveys information about processes taking place inside the organism from a different depth, which is determined by the tissue transparency for that particular radiation. Thus, the skin surface emits radiation brightly at the middle infrared (IR) range of 2–20 µm, with the maximum intensity occurring at 8–14 µm. The characteristic probing depth in this case is about 100 µm. The temperature of this layer is modulated by a network of capillary blood flow (microcirculation) in the skin. Therefore the brightness of the IR radiation of the skin surface reflects skin capillary blood flow—one of the main thermo-regulatory mechanisms of living organisms.

Employment of the organism's own IR radiation is expedient, however, only for those investigations where relatively slow processes of the skin are under scrutiny, since the characteristic thermo-projection time from the depth of about 0.5 mm, where the nearest capillary layer is located, to the radiating surface layer (<100 µm) takes up to several seconds.

Deeper probing depth and consequently higher time resolution can be achieved by an active system of investigating blood distribution at the near surface tissues. By employing illumination by radiation as described in Godik, E. E., Guljaev, Yu. V., "The Human Being Through 'Eyes of Radiophysics'", Journal of Radio Engineering (Russian) 1991, No. 8, pp. 61–62, a picture of radiation in the near IR to visible red range is recorded. A temporally and spectrally dynamic picture of the back scattered radiation coming from a depth of up to 1 cm can be formed in such a case which characterizes the functional redistribution of physiological pigments, mainly forms of hemoglobin. Thus, at 0.6–1.3 µm, dynamic images of back scattered radiation captured in real time reflect functional microcirculation and cell metabolism via the corresponding absorption bands of hemoglobin and cytochrome aa3 permitting, thereby, the ability to reveal the earliest functional disturbances At wavelengths greater than this, tissue is no longer transparent due to absorption of radiation by water. Visible radiation used in such a case is quite near to the natural background illumination both in intensity and spectral composition.

This method, however, has a number of disadvantages. Measuring back-scattered radiation gives information only on less dynamic physiological parameters such as blood content, but not arterial blood flow, as in IR thermovision. This method also is less sensitive to inflammatory processes in the near surface tissues connected with extra thermo-production. All this limits the possibility of revealing and identifying functional disturbances of the capillary blood supply network.

Some of the disadvantages of this method of investigating skin microcirculation can be overcome by recording images of living tissue at several spectral regions, more precisely at the 10–12 µm range of emitted IR radiation and in the visible spectral range. This permits superimposing the images on a display allowing the addition of details from both images in a single display as described in Ring, E. F. J. and Hughes, H. "Real Time Video Thermography", in Recent Developments in Medical and Physiological Imaging a supplement to Journal of Medical Engineering and Technology, 1986, pp. 86–89. Under these conditions, the image obtained from the spectrum is displayed as a monochrome image and the superimposed IR image is displayed in false color. This method permits localization of heated or cooled tissue on the visible topographic map formed by the visible spectrum and thereby maps the differences in blood flow onto the skin's surface.

A functional scheme of a double-channel set-up for the realization of the above set-up includes a thermovision system based on a commercially available product connected to a computer interface board. The set-up also has an illumination source, an ordinary video camera, and a means to combine the thermovision images with the video images at the display of the video controller.

This method also has considerable disadvantages. In this example, mapping is performed with the use of a video camera to improve the spatial resolution of the investigated region. Under these conditions, useful information regarding the dynamics of the tissue blood supply contained in the image in the visible and near IR spectral regions is absolutely lost. It is also known that images recorded at narrow spectral ranges carry information on the degree of blood oxygenation, hemoglobin and cytochrome aa3 content. Also, as will be shown later, employment of different wavelengths of the visual spectral range permits visualization of skin microcirculation at different depths from the surface. In the method under consideration, spatial-temporal microcirculation dynamics are reflected only in the infrared thermovision data which limits the information to coming from a tissue thickness of not more than 1 mm. Blood flow changes are projected via thermal conductivity into a very thin (less than 100 μm) layer on the epidermis. This layer itself does not contain blood capillaries, but only radiates IR radiation in accordance with the thermo-projected temperature distribution. Also, this method of visualizing microcirculation dynamics is an inertial one, since the thermo-projection time is several seconds.

It is therefore an object of this invention to increase the volume of information obtained regarding spatial-temporal microcirculation dynamics by the following means:

Increase the probing depth up to 3–5 mm or more, while estimating the contributions of layers at different depths.

Separate the partial contributions of hemoglobin in various functional forms, as well as other intercellular pigments and water located in the intercellular space.

Achieve non-inertial visualization.

Determine new physiological parameters which characterize the microcirculation state, for example microcirculation working cross-section.

It is a further object of this invention to accomplish the above by recording at least one additional parameter which characterizes the interconnection between blood content and capillary blood flow and accomplishes a functional diagnosis of microcirculation of physiological liquids in the skin. An example of this is provided in the present invention by the sequential recording of the IR radiation emitted by the skin with simultaneous recording of scattered or specifically backscattered light at visible and near IR wavelengths under conditions of external illumination over the same region with subsequent superimposition of the images obtained thereby. The parameter to be measured is the relationship between the temporal changes in scattered/backscattered light in at least one of the spectral ranges of 0.3 to 2.0 μm and changes in intensity of emitted IR radiation. This parameter is represented in the form of spatial-temporal distribution within the boundaries of the image region under investigation.

SUMMARY OF THE INVENTION

Within the aforementioned spatial-temporal distributions attained with the present invention, spatial ranges are revealed which differ from each other by at least one parameter which characterizes their temporal changes. A set of such ranges with a similar type of temporal dynamics of the recorded parameter represents a functional map the living organism's physiological processes.

External illumination is performed using a light beam, with the distance between the illumination input point and the detection point being periodically changed. The brightness distribution of the acquired image is recorded synchronously with the frequency of the distance changes.

This invention includes an illumination source and transducers which convert backscattered visible and near IR and emitted IR radiation into electrical signals and a computer which acquires the data and controls the apparatus. The backscattered visible and near IR and emitted IR radiation are focused by means of common optics fitted with a zoom control and a visible/IR beam splitter under the control of the acquisition computer. Both visible and near IR and IR video channels are connected to the computer via video scan conversion modules and video input (digitizing) boards. The illumination source, the video scanning system and the video input circuits are all under computer control.

An analog switch circuit could be used to select between the visible and near IR and IR video signals to enable one set of scan conversion and digitizing circuits to be used for both signals. Discrete photodetectors could be used to form the video signal, or alternatively, an array of photodetectors could be used.

A circuit to modulate the illumination frequency and synchronize each photodetector could be additionally included in the apparatus. The modulation circuit would be connected to the input of the illumination control and the video scan conversion circuits.

Alternatively, a device to modulate the wavelength of detected radiation could be placed in the visible and near IR path of the photodetector. This modulator is connected to the input controller to synchronize the input.

The illumination source and/or the photodetectors can be supplied with a driver to produce periodical changes in the distance between them. This circuit is connected to the input circuit to synchronize the input.

The optical apparatus can be equipped with an additional photodetector, logarithmic amplifiers and a differential amplifier. The photodetector and illuminator are placed at the image plane of the system. A circuit is included to allow the video scan conversion circuit to select between inverting and non-inverting outputs from the differential amplifier.

The optical apparatus can be a multichannel spectrometer, made up of polychromators and photodetectors connected to logarithmic amplifiers followed by differential amplifiers connected to video input circuits as above. In this case the living tissue under investigation would be illuminated by white light.

In another alternative design, the visible and near IR illumination could be provided by two line sources arranged parallel to each other along with two multi-element lines of photodetectors. The photodetectors are connected to differential amplifiers and video scan conversion circuits via logarithmic amplifiers. In this case the IR channel photodetector would also be a multielement array, placed parallel to the lines of the visible and near IR channel and connected to a video scan converter via a multichannel amplifier.

For a better understanding of the present invention, together with further and other objects, reference is made to the following description taken in conjunction with the accompanying drawings, and its scope will be pointed out in the appended claims.

DETAILED DESCRIPTION OF THE PREFERRED EMBODIMENTS AND METHODS

Figure 1:
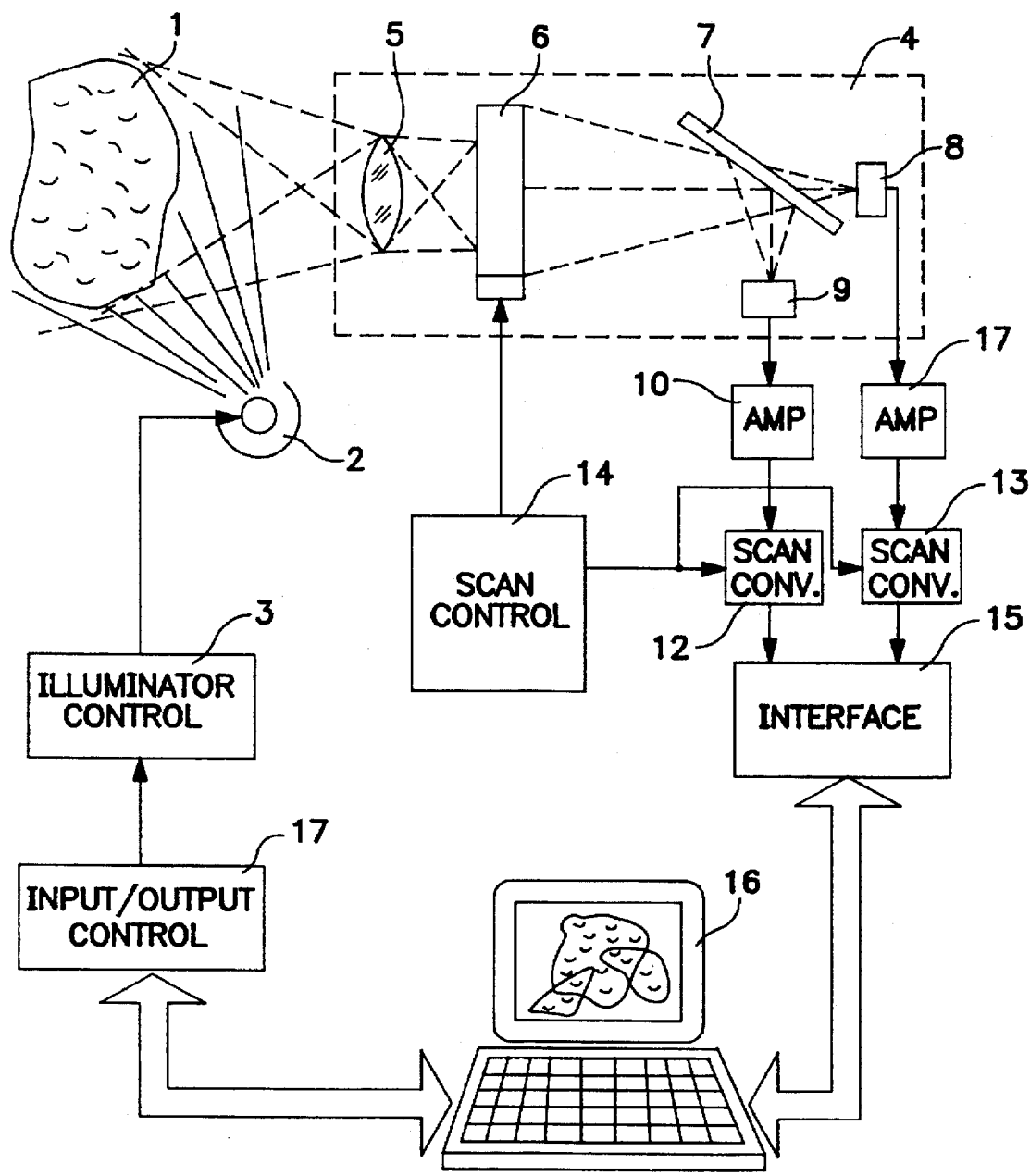
FIG. 1 is a schematic block diagram of an apparatus for realization of this invention.

As was mentioned above, simple image superimposition, which is equivalent to the linear combination of visible and near IR and IR images, only in an insignificant degree reflects the real interconnection existing between capillary blood content and capillary blood flow. Recall that blood content is shown by contrast in the visual image and blood flow is shown by contrast in the IR image. In reality the dynamics of the IR image is influenced not only by the arterial and venous circulation of blood but also by the presence of "stagnant reservoirs", "shunting", or "blocked" capillary blood flow areas which are determined by the contrast of the visible image. The resulting connection between the IR and visible and near IR images is considerably non-linear and depends upon the functional state of the living tissue being investigated. Consequently, processing methods which reveal these non-linear "interference" parameters of connectivity between the IR and visible images yields information which could not be obtained separately from either of the component images or their simple linear combination. This non-linear component exists not only between corresponding points in the IR and visible images at any specific time, but also between different points at each time interval or even between different points at different times. This level of correlation can be revealed by means of special software designed to perform factor or cluster analysis as described in Platonov, S. A., . . . , Godik, E. E., "Informative Tasks of Functional Mapping of Biological Subjects", *Journal of Radio Engineering* (Russian) 1991, No. 8, pp. 62–68. Functional images (maps) thus obtained reveal new information regarding the functioning of living tissue or about the hierarchy of interconnected subsystems which could not be obtained without the combination of IR and visible and near IR images and consequent computer processing.

Fast (less than one second) blood vessel reactions to any external influence are revealed first of all by the visible brightness: when the vessels constrict (dilate) the visible image brightness decreases (increases). In addition, the volume of blood flowing through the (blood) vessel changes since the diameter is changed, while the pressure at the main artery in unchanged. As a result, blood flow is correspondingly changed and variations in the dynamics of IR image appear with a time delay of several seconds equal to the above mentioned thermo-projection time. In the presence of some physiological disturbances, the synchronous behavior of IR and visible and near IR image brightness is broken, and as a result the ratio of the two images is no longer constant. Examination of this ratio permits localization and characterization of the (blood) vessel's pathology.

Another example characterizing the above mentioned interconnection is the time delay between the equivalent parts of the temporal dynamics of IR and visible and near IR image brightness when it exceeds the above mentioned thermal-projection time.

If the spatial distribution of the extremes for each curve are plotted as a function of each time interval (t), a third type of parameter characterizing the interconnection between the IR and visible and near IR images is formed.

Artifacts (irrelavent information) due to blood microcirculation (or any other physiological liquid) at some depth from the skin's surface can be eliminated modulating the wavelength ($\lambda$-modulation) of light. Such artifacts could be created by light reflecting from the surface, fluctuations in the illuminating light's intensity, $I_o(r,t)$, by extraneous illumination, by skin pigmentation, by light scattering in the epidermis, or by non-uniformity in the light-shadow distribution, $F(r,t)$. This method of $\lambda$-modulation includes recording the differences in intensity distribution for the reflected light at two different wavelengths. The wavelengths are chosen so that physiological pigments (hemoglobin, for example) have significantly different absorption characteristics and consequently different diffusive reflectivity. This diffusive reflectivity is described by a function f. If these wavelengths are not considerably different, then, since the effect of the above described factors is only slightly dependent upon wavelength, their spectral dependency could be neglected. Then:

$$I(r,t)=I_o(r,t)*F(r,t)*f(\lambda,c,r,t)$$

and $$dI_{\lambda 1,\lambda 2}=I_o*F*df$$

where r, t (spatial and temporal distributions, respectively) are factors independent of $\lambda$, c is the physiological pigment concentration. The ratio $dI/I=df/f$ then describes only the pigment investigated.

Recording the visible and near IR images at discrete wavelengths enables this technology to measure several additional parameters. It is possible to separate several spectral intervals where the greatest difference in absorption coefficient, coefficient of back scattering and reflective capability take place by taking into consideration the spectral dependence of the reflective capability ($R=I/I_o$) of biological tissues as described in Jacquez, J. A. et al, "Spectral Reflectance of Human Skin in the Region 235–1000 nm", *Journal of Applied Physiology,* 1955, Vol. 7, No. 3, pp. 523–528. At the spectral range under consideration, the reflective capability is determined only to a small extent by Frenel surface reflection ($R_{sur}=4-6\%$). The main contribution is made by back scattered radiation ($R_{back}$) from tissues at depth, where the main physiological pigments (hemoglobin and water) are located. The signal back-scattered from tissue blood can be most clearly imaged by modulating the illuminating radiation at the spectral ranges which are absorbed by physiological pigments, since the visible absorption of the epidermis is small and only slightly depends on the radiation wavelength. The λ-modulation of illuminating radiation results in amplitude modulation of the radiation back scattered from the tissues containing physiological pigments. The latter radiation is recorded by synchronous detection at the modulation frequency of the illuminating radiation. Under these conditions the spectral band employed must be less than the frequency of the interval over which the modulation is performed.

To record the total oxygenated and deoxygenated hemoglobin content in tissues of up to 3 mm depth, the radiation frequency is modulated at a spectral range near 0.59 μm, the minimal wavelength being chosen at 0.52 to 0.58 μm and the maximal one from 0.60 to 0.63 μm. The 0.52 to 0.58 μm range corresponds to the long wavelength hemoglobin absorption band. To record hemoglobin content at a lesser depth, the modulation is performed near 0.43 μm wavelength, with the minimal wavelength being chosen at the 0.38 to 0.43 μm band (the Sore band of hemoglobin absorption) and the maximal one being 0.46 to 0.50 μm.

To record the partial concentration of deoxygenated hemoglobin, the wavelength modulation is performed near 0.68 μm, where oxygenated hemoglobin absorption is minimal. The modulation frequency is from 0.63 to 0.72 μm.

The interval from 0.8 to 0.9 μm is chosen for the reference wavelength since hemoglobin absorption is minimal and does not depend upon the degree of hemoglobin oxygenation, while the reflective capability is maximal.

To record water concentration in near surface tissues under conditions of uniform illumination at depths up to 3 mm, a wavelength near 1.15 μm is modulated over the interval from 1.1 to 1.2 μm.

Water content near the surface of the skin, at the horny epidermis layer, could be estimated via the absorption at a spectral window of 1.6 to 1.8 μm, modulated from reference wavelengths of 1.4 μm and 1.9 to 2.0 μm, since the reflective capability is minimal and is determined practically by Frenel's surface reflectivity.

Of special interest is the possibility of hematocrit estimation calculated by the ratio of hemoglobin and water concentrations in near surface tissues. This is performed by comparing the results of hemoglobin concentration measurements from the spectral range of 0.53 to 0.63 μm with those for water from the spectral range of 1.1 to 1.2 μm. At those wavelengths the reflected radiation is formed by back scattering in tissues of practically the same thickness. In the same fashion, hematocrit can be estimated when the results of hemoglobin concentration measurements taken at 0.38 to 0.50 μm are compared to those for water taken at 1.3 to 1.4 μm.

Rather than modulating the illuminating radiation, it is possible to use a wide band illumination source having a bandwidth wider than the desired spectral band and modulate the receiving spectral band of the photodetectors instead. The result of this method is completely equivalent to the foregoing methods involving illuminating wavelength modulation.

This invention can be best implemented by means of the apparatus shown in schematic form in FIG. 1. It should further be realized that for ease of understanding the various embodiments of the present invention, like elements of this invention will be identified by similar reference numerals throughout the description of all of the figures of the drawings. Surface (skin) 1 of a subject is illuminated by means of electromagnetic source or illuminator 2, managed by the illuminator control block 3, which permits regulation of the illumination brightness (intensity) and spectral composition (wavelength). Radiation, scattered or specifically backscattered by the subject surface, as well as the subject's own IR radiation are recorded by detecting device 4. This device includes an input optical scanning system which includes a focusing element 5, scanning mechanism depicted by block 6, and a selective divisor or beam splitter 7. Radiation in the IR channel is recorded by photodetector 8 and that of the visible and near IR channel by photodetector 9. Elements 5 and 6 are capable of transmitting both the IR and visible and near IR wavelength ranges. The beam splitter 7 transmits IR radiation and reflects visible and near IR radiation.

Electrical signals from photodetectors 8 and 9 are received by corresponding amplifiers 10 and 11 and then by corresponding video signal scan converters 12 and 13. Synchronizing pulses are brought to the video signal scan converters 12 and 13 from the output of scanning control block 14 of the scanning system. Scanning control block 14 controls scanning mechanism 6 which forms the video frames by generating horizontal and vertical timing signals.

Video signals from the two channels, formed at converters 12 and 13, are received by a computer 16 via an interface board 15. The computer 16 also manages the illumination control block 3 through an input/output controller 17.

The method of the present invention is performed as follows: To record the parameters characterizing the interconnection between blood content and blood flow, a subject is illuminated by electromagnetic radiation from the source 2, the radiation wavelength being at one of the aforementioned wavelengths in the range 0.3 to 2.0 μm. The radiation reflected, that is, backscattered by the subject's surface 1, together with IR radiation emitted by the subject is received via the focusing element 5 by the scanning mechanism 6 and is divided by beam splitter 7 into two beams. One beam (IR) is received by photodetector 8 and the other (visible) and near IR is received by photodetector 9. Photodetectors 8 and 9 are placed so as to record radiation originating from the same point of the subject. Scanning mechanism 6 provides subsequent examination of all surface 1 points (locations), being within the range of vision of detecting system 4. The sequence of electrical signals from amplifiers 10 and 11 are divided into rows and frames by means of synchronizing pulses coming from the control block 14 of the scanning system. In this way, video signals of IR and visible and near IR wavelength images are formed at converters 12 and 13. These signals are received by the computer interface 15, transforming them into digital form and performing the functions of image input, output and image accumulation. The final image processing, i.e. functional map construction, is performed by the computer 16.

Figure 2:
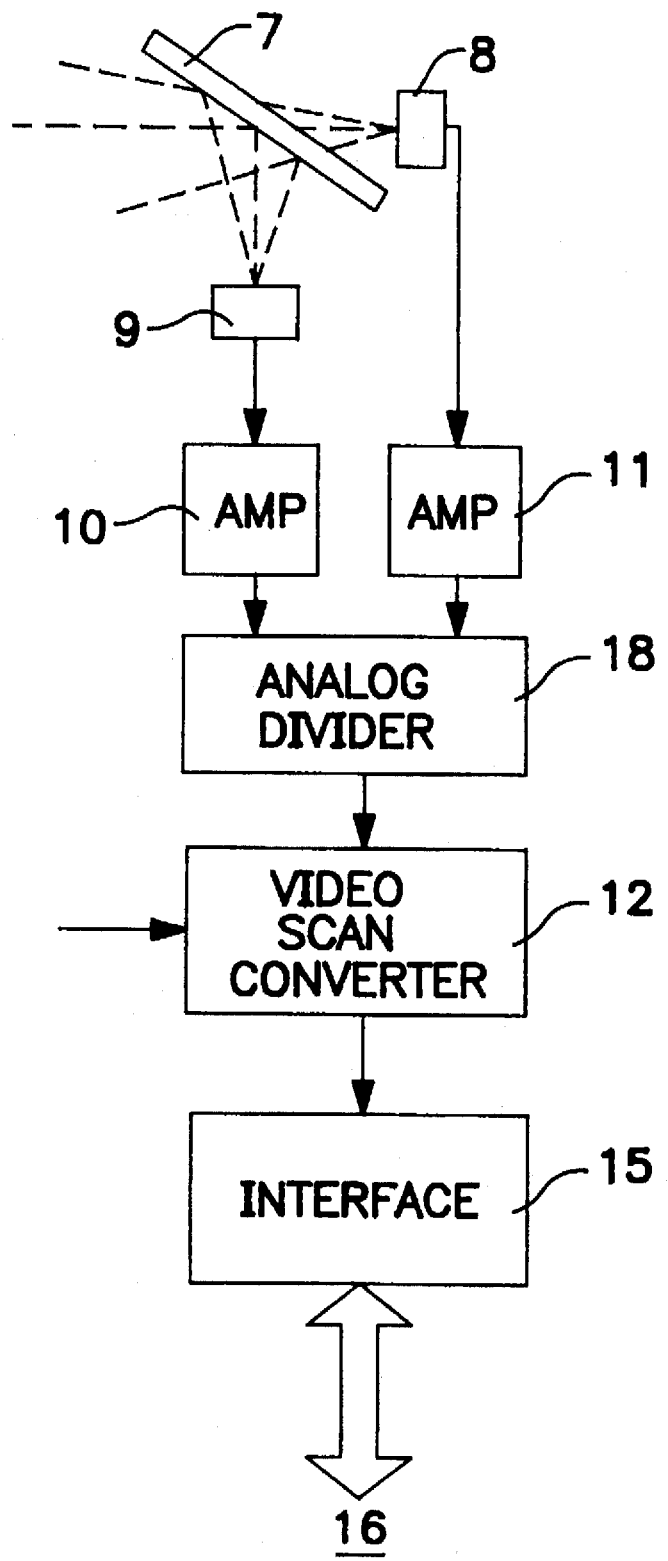
FIG. 2 is a modification of the apparatus shown in FIG. 1 with improvements to the signal conditioning circuits.

FIG. 2 shows a variant of the method for signal processing. This variant is distinguished by its use of an analog divider 18. This divider 18 is placed between the outputs of amplifiers 10 and 11 and the input of the video scan converter 12. The divider 18 is designed to calculate the ratio of amplitudes of the emitted IR and backscattered visible and near IR signals. In this case, an image is formed on the computer display which describes the temporal changes of infrared radiation intensity as compared with those of the visible and near IR image for each surface point or location.

Figure 3:
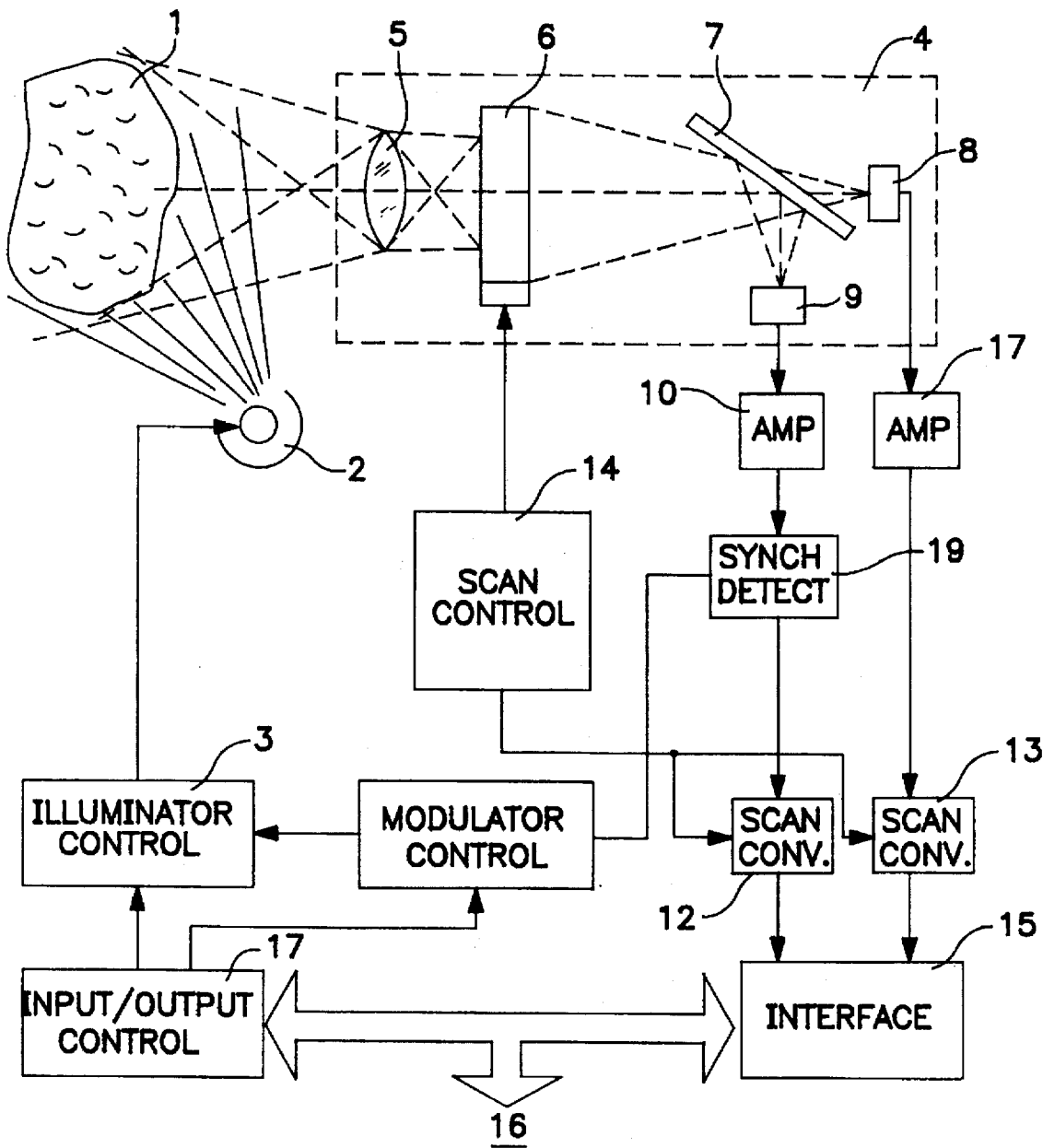
FIG. 3 is a schematic representation of the invention employing spectral modulation and synchronous detection.

FIG. 3 shows an alternate method of image recording using illuminating radiation modulation and synchronous detection. To implement this method, the illuminator or source of electromagnetic radiation 2 is directed by control block 3 to alternately radiate light of wavelengths $\lambda_1$ and $\lambda_2$ at a frequency $f_m$. The actual values of $\lambda_1$ and $\lambda_2$ are chosen to select the depth to be recorded, as described above. The modulation frequency must be higher than the inverse of the time required to scan a single pixel in the final video image formed. Thus, for a 128×128 matrix being scanned at 50 Hz, the time for a single pixel would be approximately 1.2 µs, therefore $f_m$ should be larger than 1/1.2 µs, or 3 to 5 MHz.

Between the output of amplifier 10 of the visible channel and input of the corresponding video scan converter 12, a synchronous detector 19 is included. A reference signal 17, synchronous with the frequency $f_m$, is formed by modulator 20 based on input received from detector 19, and this signal is connected with the input of control block 3. Control block 3 separates signals of frequency $f_m$ with the amplitude being proportional to the wavelength of the derivative of the reflectivity coefficient of light. When the appropriate spectral interval is chosen, this signal brings information on the dynamics of concentration changes in the corresponding blood component. These components include oxy- and deoxy-hemoglobin, cytochrome aa3, and water.

Figure 4:
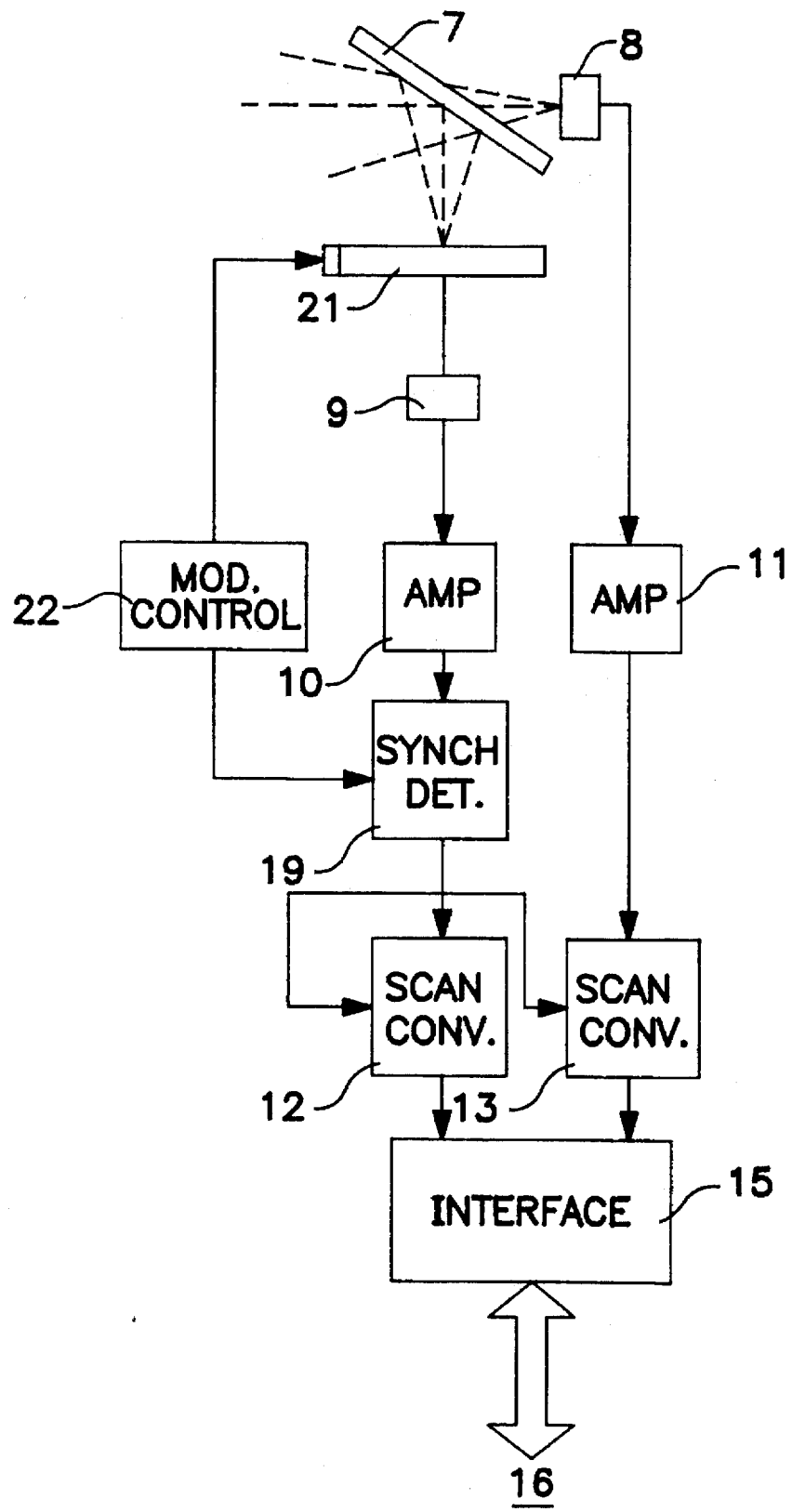
FIG. 4 is a schematic representation of the invention employing modulation of the detected radiation spectrum with synchronous detection.

FIG. 4 presents a recording system employing spectral modulation of the recorded illumination and synchronous detection of a wide band illumination source. To realize this aspect of the invention, a modulator 21 is placed before the input of photodetector 9 in the visible and near IR channel connected to modulator control block 22. A synchronous detector 19 is included between amplifier 10 output and input of the corresponding video scan converter 12. This detector 19 is controlled by an input from the modulator control block 22. This method functions similarly to that shown in FIG. 3.

Figure 5:
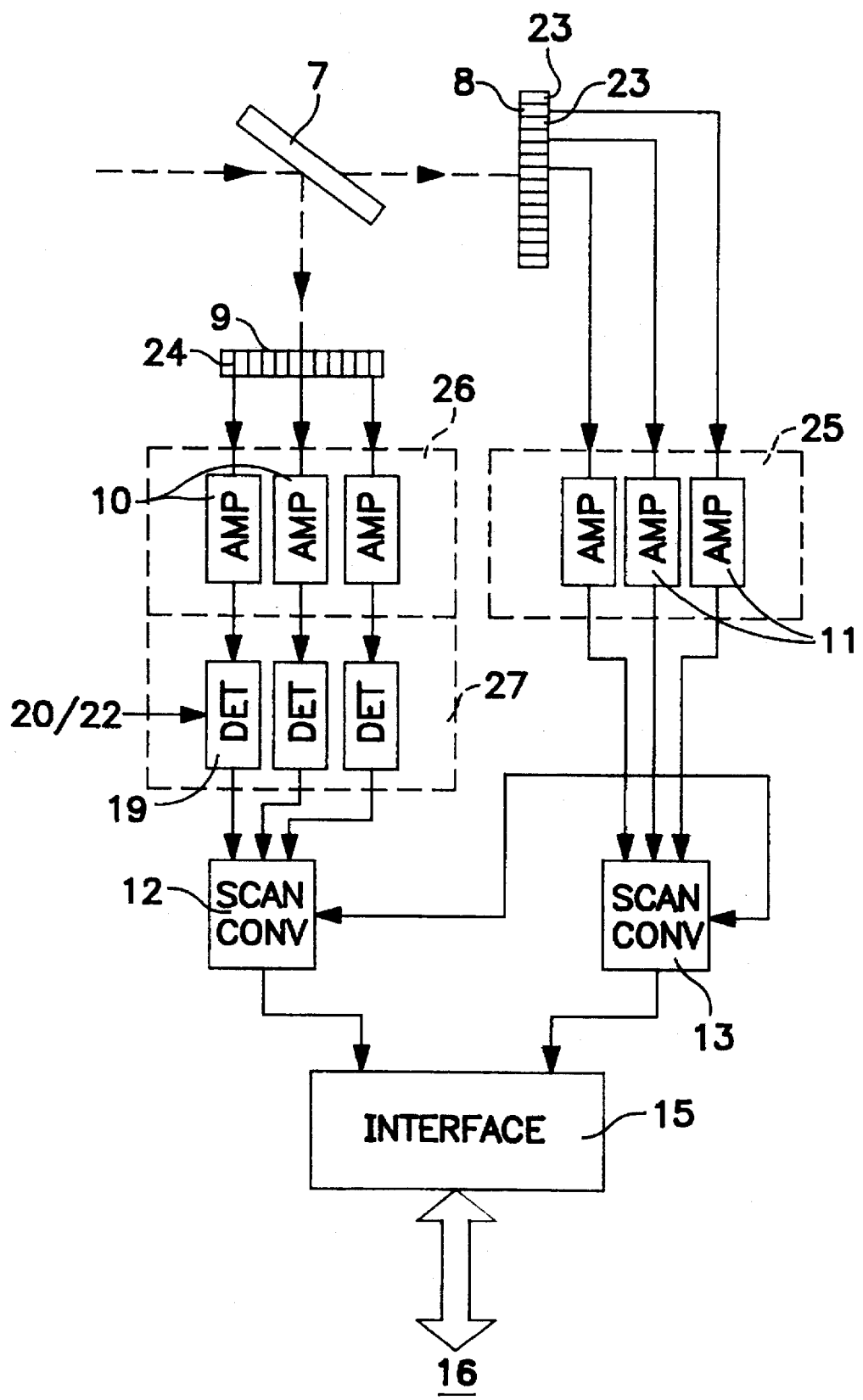
FIG. 5 is a schematic representation of the invention using arrays of photodetectors.

FIG. 5 shows a recording system employing arrays of discrete photodetectors. This aspect of the invention permits simplification of the scanning block, enabling the beam to be scanned over the array of photodetectors in one dimension rather than two as would be the case with a single detector. In the case where a two dimensional array of photodetectors are used, the scanner could be excluded completely, or a mechanical scanner with a much lower rate may be used. Photodetector 8 of the IR channel is an array of discrete photodetector elements 23, and photodetector 9 of the visible and near IR channel is array of elements 24. Outputs of array elements 23 and 24 are connected to inputs of multichannel amplifiers 25 and 26. The outputs of amplifiers 10 of multichannel amplifier 26 are connected to inputs of multichannel synchronous detectors 27, consisting of detectors 19 formed into modulator control block 22. Outputs of detectors 19 are connected to inputs of the video scan converter 12 of the visible and near IR channel.

Figure 6:
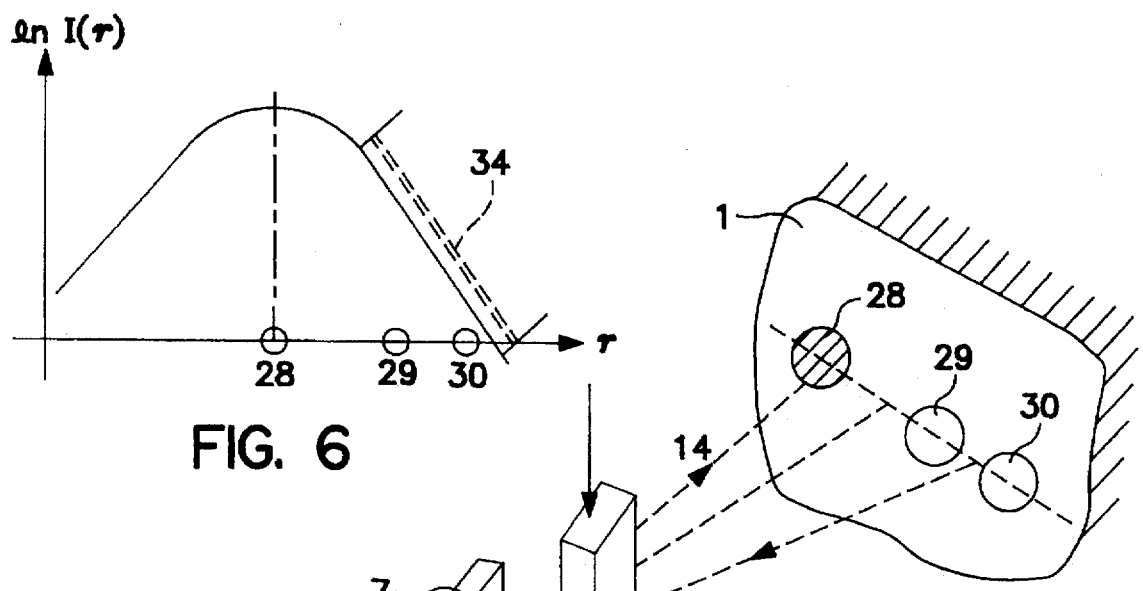
FIG. 6 is a graphic representation of the distribution of scattered light intensity over the input point of the illuminating beam as provided by this invention.
Figure 7:
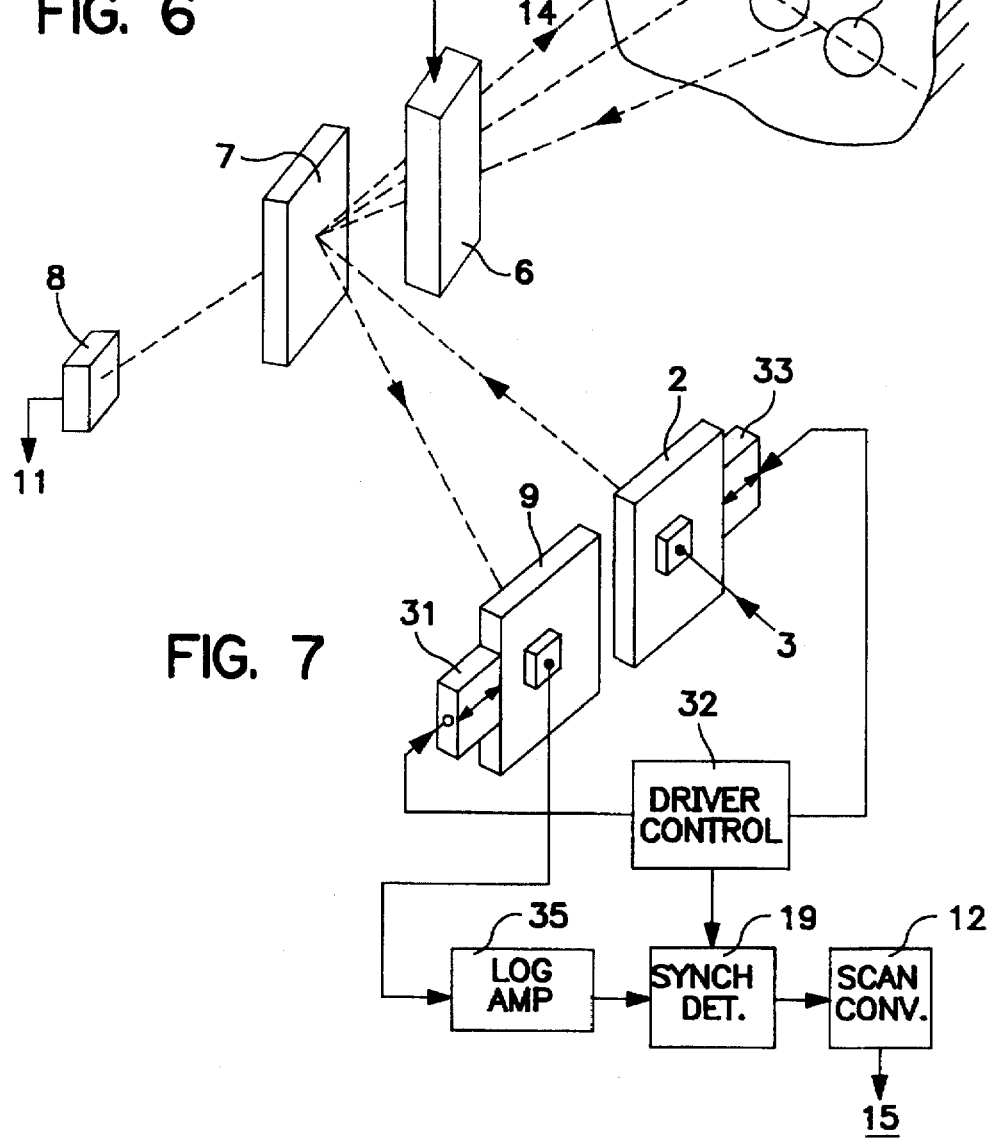
FIG. 7 is a pictorial, schematic representation of the invention illustrating a modulation of the observation point coordinate.

All of the following descriptions of the present invention are based on a strong dependence of the scattered/backscattered radiation intensity on the distance between the input point of the illuminating beam and the point of the scattered/backscattered light output (the observation point.) For this purpose the illuminator, contrary to the variants with uniform illumination as shown in FIGS. 1–3, forms light beams of varying intensity. FIG. 6 shows a diagram of the intensity distribution I(r) where an input point of the illuminating beam is marked by 28 and the observation point by 29. By choosing the observation point shifted relative to the illumination point by several photon transport lengths in the tissue investigated (typically more than 5 mm), and by periodically changing the distance between these points, it is possible to receive a signal at the modulation frequency which depends only on the state of the blood content of the layers of tissue at the desired depth and reject spurious signals from scattering and absorbency at the tissue surface. It is possible to vary the distance distance between points 28 and 29 by two means: by shifting the illuminating beam while the observation point is fixed or vice versa. Under these conditions the observation point of the IR channel should be located between the input and the observation points. The case of changing the observation point is shown in FIG. 7. Moving the observation point from one outermost position 29 to the other 30 is performed by moving the photodetector at the image plane by the corresponding distance. Such movement could be accomplished by means of a linear driver 31, connected to the driver control block 32. A similar driver 33 may also be connected with the illuminator 2, in which case the driver 31 should be switched off. Illuminator 2 and photodetector 9 of the visible channel are located at the image plane.

Observation point 29 must be shifted relative to point 28 in FIG. 7 in such a way that the point of the scattered/backscattered light received is located at the exponential part of the I(r) function (position 34 of FIG. 6). Function I(r) can be expressed in analytic form as:

$$I(r)=I_o*f(r, K)*\exp[-K(r-r_o)]$$

where $$K = \sqrt{3 G_{ab} G_{sc} N^2}$$

and $G_{ab}$, $G_{sc}$=effective absorption and scattering cross-sections of erythrocytes N=erythrocyte concentration $f(r,K)$=a function slightly dependent upon the beam coordinate Then:

$$\ln[I(r)]=\ln[I_o]+\ln[f(r,K)]-K(r-r_o)$$

When the coordinate of the observation point is shifted by $\Delta r$, then the corresponding change in $\Delta \ln[I(r)]$ is as follows:

$$\Delta\ln[I(r)]=\Delta I(r)/I(r)=-K*\Delta r$$

Consequently, measurement of $\Delta\ln[I(r)]$ by modulating coordinate r permits calculation of parameter K as well as the related parameter erythrocyte concentration. This means that the logarithm derivative of the reflected signal permits determination of parameter K and thereby the state of microcirculation of physiological liquids at the tissue layer under investigation.

Still referring to FIG. 7, for a technical realization of the logarithm derivative, the signal at the frequency of the modulation comes to logarithm amplifier 35 connected with synchronous detector 19 and then, as in previous variants shown in FIGS. 3–5, to the video scan converter 12. In this case the reference signal for the detector 19 is produced by the driver control block 32.

Figure 8:
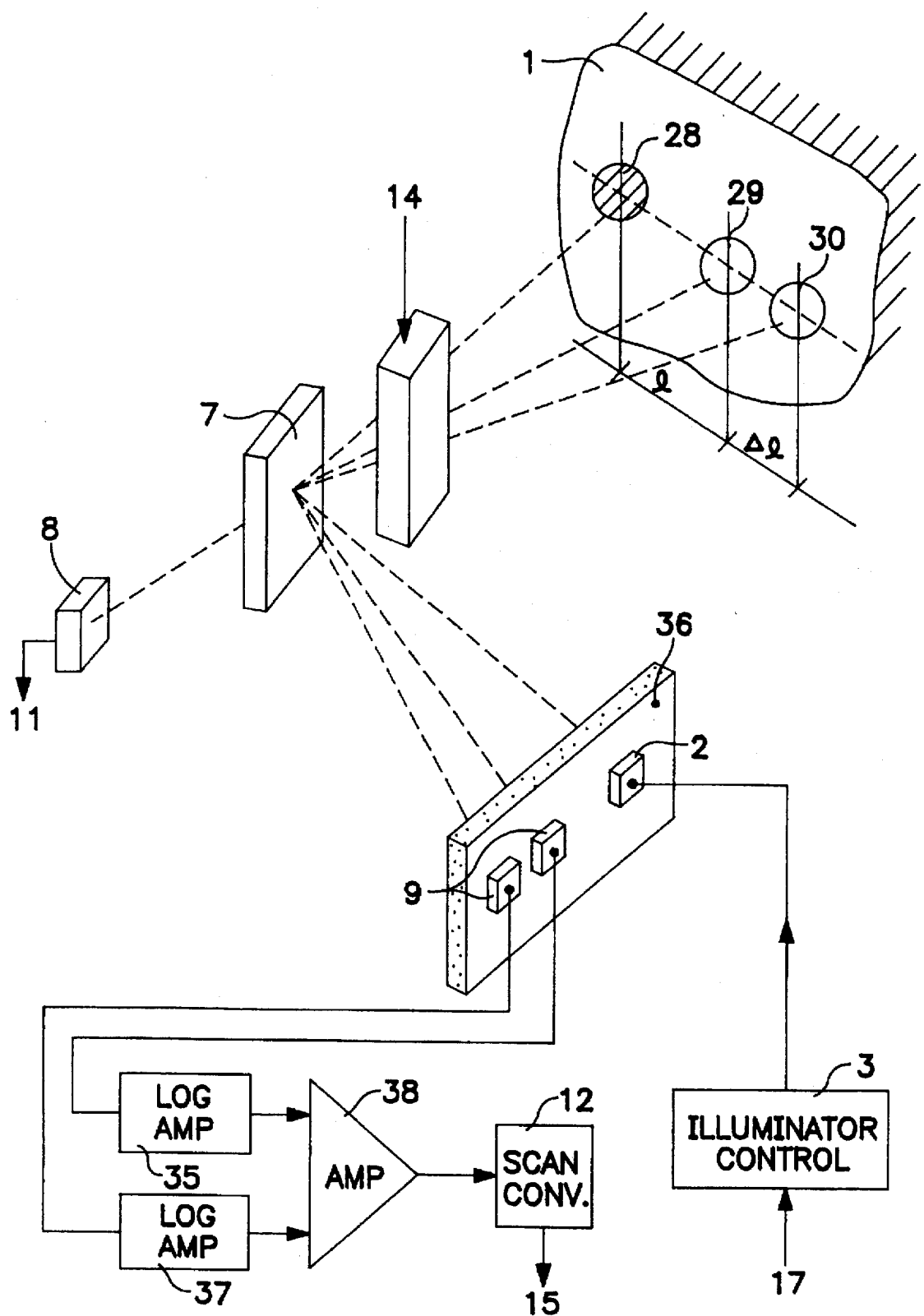
FIG. 8 is a pictorial, schematic representation of the invention illustrating the use of a differential photodetector.

In FIG. 8, a further embodiment of the apparatus of FIG. 7 is shown where the logarithm derivative is calculated by a differential photodetector. The differential photodetector contains two on-element photodetectors 9 fixed by holder 36 together with illuminator 2, both of which are place at the image plane. The distance between the photodetectors are chosen so that the observation points 29 and 30 are separated by a distance $\Delta r$. Photodetector 9 outputs are connected with logarithmic amplifiers 35 and 37. Outputs of the logarithmic amplifiers 35 and 37 are connected with inverting and non-inverting inputs of the differential amplifier 38, with the output of the latter being coupled with the video scan converter 12.

Thus, the measurements employing differential photodetectors give information about parameter K. In this case, unlike that shown in FIG. 7, the use of λ-modulation is more convenient and straightforward. Under these conditions the detection is performed at the frequency of λ-modulation, unlike the previous case where it is carried out at the beam spatial modulation frequency. When the method utilizing the apparatus as shown in FIG. 7 is employed, the combination of the two modulation modes is possible if the frequencies of the modulation are sufficiently different and a double synchronous detection is carried out.

Figure 9:
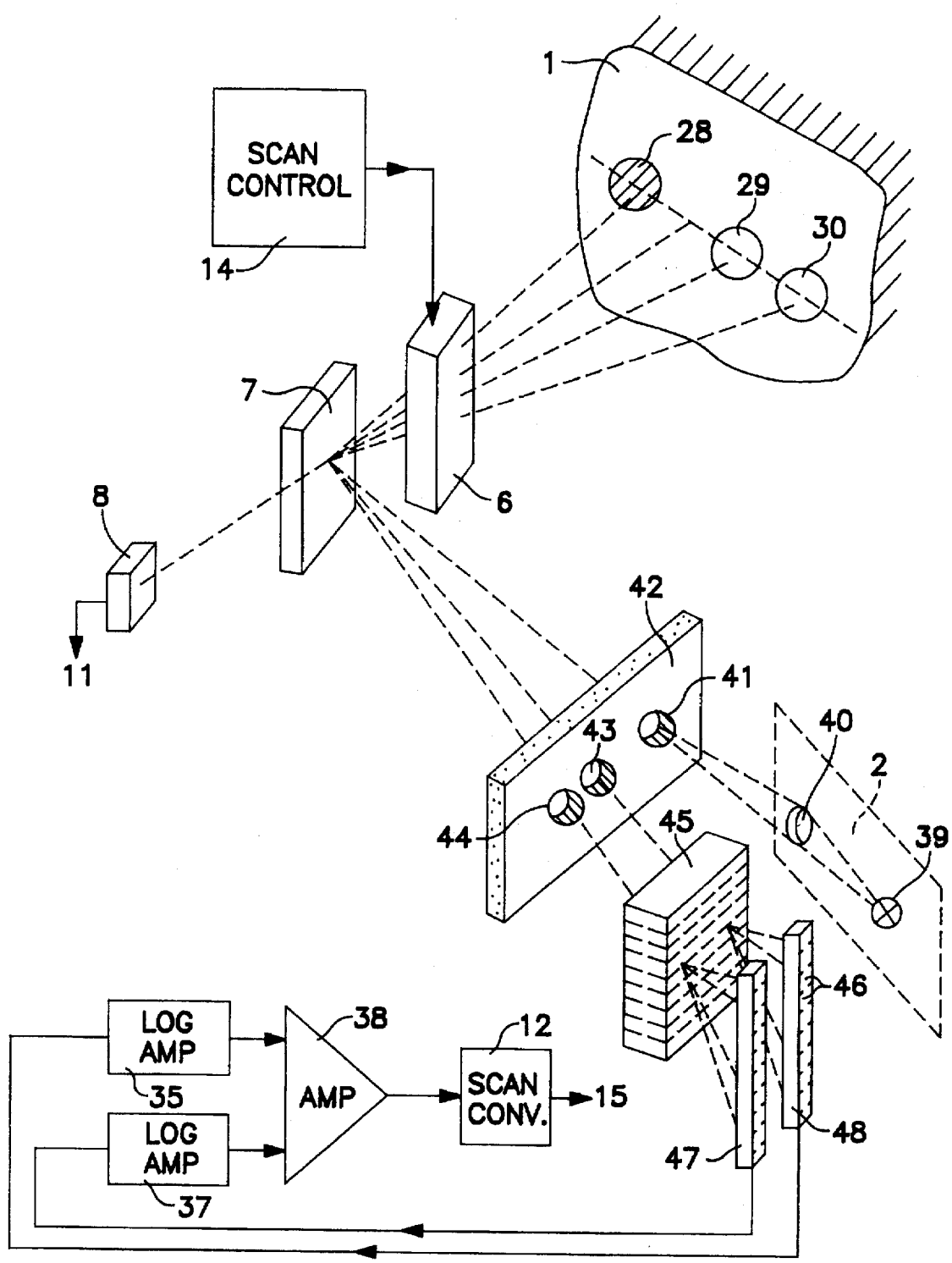
FIG. 9 is a pictorial, schematic representation of the invention illustrating the use of a polychromator and multielement differential CCD structures.

FIG. 9 shows the apparatus of this invention utilized for a recording method including a polychromator and differential multielement photodetectors based on CCD structures. This method makes it possible to obtain temporal behavior of the reflected light not only at some fixed wavelength, but also in a wide spectral range. As a result, separation and identification of the contributions to the total signal from different components of physiological liquids could be obtained, for example imaging the distribution of some medicinal solutions. A wide spectral range of the illuminating radiation is produced by illuminator 2, consisting of a white light source 39 and lens 40. The latter focuses light from the illuminator into an input hole 41 in plate 42, which is located at the plane of the detector image. An image of this input hole 41 at the surface 1 of the subject being investigated is the illuminating beam input point 28.

Output holes 43 and 44 correspond to observation points 29 and 30; it is via these holes the light beams come to polychromator 45. After coming through the polychromator 45, the white light is separated into spectral components spreading in different directions. Each of such components is recorded by array elements 46 of multielement photodetectors 47 and 48. Each of the photodetectors 47 and 48 is connected with logarithmic amplifiers 35 and 37, the outputs of the latter being connected with inputs of the differential amplifier 38. Further, as in previous embodiments of this invention, the signal is received by a video scan converter 12 and so on.

Figure 10:
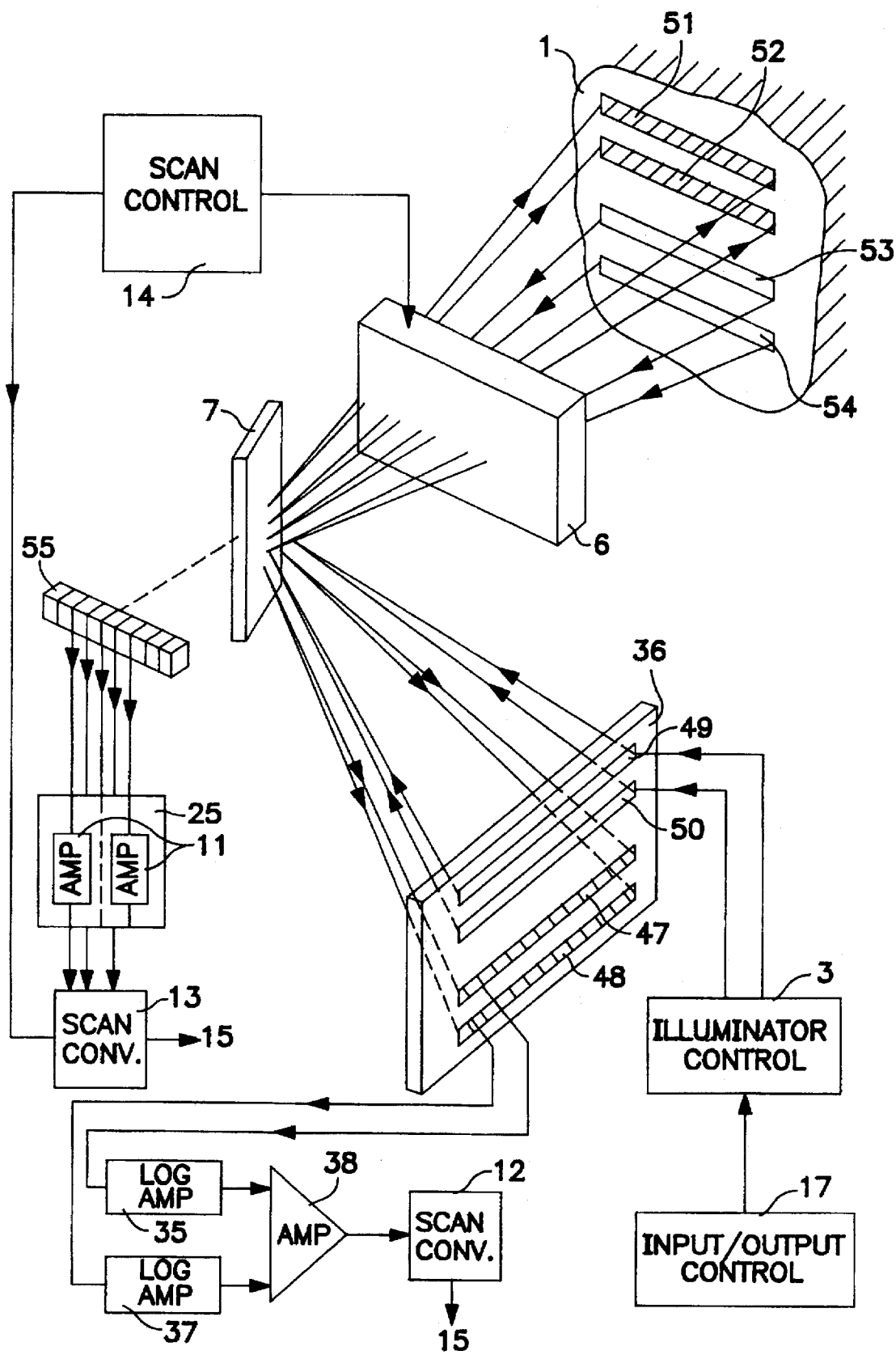
FIG. 10 is a pictorial, schematic representation of the invention illustrating an array of illumination sources and corresponding photodetectors.

FIG. 10 shows a further embodiment of the apparatus of this invention employing one-dimensional illuminations sources and detectors. Such a device makes it possible to avoid the necessity of row scanning and uses only frame scanning, since at each time moment recording of two lines of a video scan—the main and the differential (shifted at the objective plane relative to the main) is performed. This method makes it possible to reduce the time required to record a frame and thereby permits recording of fast physiological processes, or can improve signal-to-noise ratios while frame recording time is held constant. In addition, avoiding row scanning results in a simpler, more reliable, more easily synchronizable electro-optical system.

In the embodiment of FIG. 10, a pair of lines of illuminators 49 and 50, radiating electromagnetic radiation at wavelengths $\lambda_1$ and $\lambda_2$, correspondingly, as well as a pair of lines of photodetectors 47 and 48 are fixed by means of holder 36, located at the image plane. The distance between lines of photodetectors 49 and 50, 50 and 47, and 47 and 48, respectively, are chosen so that the shifts at the plane of the subject between images 51 and 52 iluminated by illuminators 49 and 50, respectively, as well as observation locations 53 and 54 detected by photodetectors 47 and 48, respectively satisfy the following relationships:

$$\Delta_{s1-s2} \ll K^{-1}; \Delta_{s2-s3} \sim K^{-1}; \Delta_{s3-s4} \sim (0.2-0.5)K^{-1}$$

Each of the detectors 47 and 48 is connected with logarithmic amplifiers 35 and 37, and the outputs of amplifiers 35 and 37 are connected to the inputs of differential amplifier 38. The signal therefrom is then passed to the input of a video scan converter 12. The lines of illuminators 49 and 50 are connected with the illuminator control block 3. In this mode, the IR detector should also be a one-dimensional multielement line, consisting of discreet IR detector elements 55, capable of recording the whole frame line at each time moment. A device to perform signal processing data from such a multielement detector is similar to that shown in FIG. 5.

At the display of the video control device or computer 16 (not shown in FIG. 10) an image of the investigated subject surface is reproduced as the background, for example in gray scale. The regions with similar microcirculatory behavior of physiological liquids in skin are marked with the help of pseudo-colors. The distribution of the color brightness reflects the distribution of the corresponding pigment concentration at the near surface skin layer.

Examples of some of the specific components utilized within the apparatus of this invention are provided below, although it should be realized that other equivalent elements may also be used in place thereof within the scope of this invention. For example, optical elements of the the system must be capable of working in a wide range of wavelengths. They could be prepared from quartz, sapphire or other materials transparent in both the visible and IR wavelength ranges. As the selective divisor or beamsplitter 7, a germanium or silicon plate could be used. A dichroic mirror could also be used as such a divider. The scanning mechanism 6 could be made with traditional mirror components, which are widely used in thermovision devices such as described in "Physics of Image Visualization in Medicine", C. Webb, ed. Vol. 2, pp. 241–243.

As an interface board 15, any suitable video input/output device typically used for image input and visualization could be employed such as described in Krenkel, T. E., Kogan, A. G. and Tatatorian, A. M., "Personal Computers in Engineering", Izd. Mir, RiS, (Russian) 1989, P. 71. For example, the DT 2803-60 from Data Translation.

The illuminator control block 3, upon command from the computer 16, sets up the necessary intensity level and the spectral composition of illumination, either for one common source of electromagnetic radiation of for each of several separate sources. In coordination with the input/output controller 17 an illumination controller switches on one or another source or group of sources. This technology is well known and not part of the present invention.

To effect the push-pull motion of the illuminator 2 and/or photodetector 9 as shown in FIG. 7, a linear piezo-electric transducer may be used to achieve practically non-inertial movement at a wide shifting range as described in Dgagupov, R. G. and Erofeev, A. A., Piezo-Ceramic Elements in Instrument Designing and Automatics, Leningrad, Izd. Mashinosroenie, 1986, pp. 154–155 (Russian).

As an illumination source 2, incandescent lamps may be utilized, as well as light-emitting diodes or other sources of visible and near IR electromagnetic radiation.

Although the invention has been described with reference to particular embodiments, it will be understood that this invention is also capable of further and other embodiments within the spirit and scope of the appended claims.

What is claimed is:

1. An apparatus for investigating the microcirculation of physiological liquids in skin comprising:
   a source of electromagnetic radiation for illuminating a preselected area of the skin, said source of electromagnetic radiation provides electromagnetic radiation having a wavelength in a range of 0.3 μm to 2.0 μm;

detecting means optically aligned with said preselected area of the skin for detecting infrared (IR) electromagnetic radiation emitted from the skin and electromagnetic radiation backscattered from the skin and for outputting respective signals therefrom representative of said emitted infrared electromagnetic radiation and said backscattered electromagnetic radiation;

converting means operably connected to said detecting means for converting said signals output therefrom into video signals;

interface means operably connected to said converting means for accumulating temporal variations of said video signals during a preselected period of time in a computer as recorded video signals;

comparing means operably connected to said interface means for determining and quantifying an interrelationship between said temporal variations of said recorded video signals based upon said emitted infrared and said backscattered electromagnetic radiation; and display means operably connected to said comparing means for presenting said interrelationship between said temporal variations based upon said emitted infrared and said backscattered electromagnetic radiation in the form of a functional map of the microcirculation of physiological liquids in skin for said preselected area of the skin.

2. The apparatus as defined in claim 1 wherein said detecting means comprises means for scanning said preselected area of the skin, a pair of detectors and directing means optically interposed between said scanning means and said detectors for directing said emitted infrared electromagnetic radiation to one of said detectors and said backscattered electromagnetic radiation to the other of said detectors.

3. The apparatus as defined in claim 2 further comprising means interconnected between said converting means and said scanning means for synchronizing the video signals with respect to specific locations on said preselected area of the skin.

4. The apparatus as defined in claim 3 further comprising means interconnected between said converting means and said source of electromagnetic radiation for controlling the wavelength of said electromagnetic radiation emanating from said source.

5. The apparatus as defined in claim 4 wherein said controlling means also controls the intensity of said electromagnetic radiation emanating from said source.

6. The apparatus as defined in claim 4 wherein said control means provides an input to said electromagnetic source such that said electromagnetic radiation emanating from said source alternates between wavelengths $\lambda_1$ and $\lambda_2$ at a modulation frequency $f_m$ wherein said wavelengths are selected to distinguish preselected physiological components and to penetrate a specific depth of the skin and the modulation frequency is higher than an inverse of time required to scan a single pixel in said video image.

7. The apparatus as defined in claim 6 wherein $f_m$ is approximately 3 to 5 MHz.

8. The apparatus as defined in claim 3 further comprising means interposed between said detectors and said converting means for calculating a ratio of amplitudes of said signals representative of said emitted infrared electromagnetic radiation and said backscattered electromagnetic radiation.

9. The apparatus as defined in claim 2 further comprising a wideband source of electromagnetic radiation, a modulating means interposed between said directing means and said one of said detectors, and a modulating control means interposed between said one of said detectors and said modulating means.

10. The apparatus as defined in claim 2 further comprising means operably connected to said other of said detectors for moving said other of said detectors in order to detect said backscattered electromagnetic radiation from a location removed a specific distance from the location being illuminated on said predetermined area of said skin.

11. The apparatus as defined in claim 2 further comprising means operably connected to source of electromagnetic radiation for moving said source in order to illuminate a location removed a specific distance from the location from which said reflected electromagnetic radiation is being detected.

12. The apparatus as defined in claim 2 wherein the other of said detectors comprises a differential photodetector which includes two photodetectors being spaced apart a distance corresponding to the distance between two locations on said predetermined area of said skin from which said electromagnetic radiation is being backscattered.

13. The apparatus as defined in claim 2 wherein the other of said detectors comprises a plurality of multielement photodetectors and means are optically interposed between said directing means and said multielement photodetectors for separating said backscattered electromagnetic radiation into its spectral components, each of said components being received by separate elements of said multielement photodetectors.

14. The apparatus as defined in claim 2 wherein said source of electromagnetic radiation comprises a series of illuminating sources and said other of said detectors comprises a series of photodetectors.

15. The apparatus as defined in claim 14 wherein said one of said detectors comprises a multielement photodetector.

16. The apparatus as defined in claim 1 wherein said detecting means comprises an array of discrete detectors.

17. The apparatus as defined in claim 1 further comprising means interconnected between said converting means and said source of electromagnetic radiation for controlling the intensity of said electromagnetic radiation emanating from said source.

18. A method for investigating the microcirculation of physiological liquids in skin comprising the steps of:

subjecting a preselected area of the skin to electromagnetic radiation within a range of 0.3 μm to 2.0 μm;

detecting infrared (IR) electromagnetic radiation emitted from and electromagnetic radiation backscattered from preselected locations on said preselected area of the skin over a preselected period of time;

providing output signals representative of said emitted infrared electromagnetic radiation and said backscattered electromagnetic radiation;

providing a functional map of said preselected area of the skin based upon said signals representative of an interrelationship between temporal variations in said emitted infrared electromagnetic radiation and said backscattered electromagnetic radiation; and comparing preselected aspects of said functional map in order to provide an analysis of the microcirculation of physiological liquids in the preselected area of the skin.

19. The method as defined in claim 18 further comprising the step of varying the wavelength of electromagnetic radiation over a preselected spectral interval.

20. The method as defined in claim 18 further comprising the step of scanning said beam of electromagnetic radiation over said preselected area of the skin over said preselected period of time.

21. The method as defined in claim 20, further comprising the step of varying the wavelength of electromagnetic radiation over a preselected spectral interval.

22. A method for investigating the microcirculation of physiological liquids in skin comprising the steps of:

subjecting a preselected location on the skin to electromagnetic radiation within a range of 0.3 μm to 2.0 μm;

detecting backscattered electromagnetic radiation simultaneously with infrared radiation emitted from the skin at a multiplicity of observation points at preselected distances from the location at which the skin is illuminated;

determining a concentration of physiological pigments at a given depth of the skin by measuring the logarithm of a change in intensity registered by shifting the observation point by a preselected distance and calculating a value for a parameter which is proportional to the concentration of said physiological pigments;

determining an interrelationship between temporal variations for blood flow and blood content by measuring and comparing corresponding variations of intensities of said emitted infrared and backscattered electromagnetic radiation in a preselected period of time;

performing said measurement over a preselected area of the skin and providing output signals representative of said measurement;

converting said output signals into video signals; and displaying said video signals as a video image in the form of a functional map of said preselected area.

23. A method for investigating the microcirculation of physiological liquids in skin comprising the steps of:

subjecting a preselected multiplicity of locations on the skin to electromagnetic radiation within a range of 0.3 μm to 2.0 μm;

detecting backscattered electromagnetic radiation simultaneously with infrared radiation emitted from the skin at a preselected observation point at preselected distance from the locations at which the skin is illuminated;

determining a concentration of physiological pigments at a given depth of the skin by measuring the logarithm of a change in intensity registered by shifting the observation point by a preselected distance and calculating a value for a parameter which is proportional to the concentration of said physiological pigments;

determining an interrelationship between temporal variations for blood flow and blood content by measuring and comparing corresponding variations of intensities of said emitted infrared and backscattered electromagnetic radiation in a preselected period of time;

performing said measurement over a preselected area of the skin and providing output signals representative of said measurement;

converting said output signals into video signals; and displaying said video signals as a video image in the form of a functional map of said preselected area.

\* \* \* \* \*